United States Patent [19]

Langhorst

[11] Patent Number: 5,235,843
[45] Date of Patent: Aug. 17, 1993

[54] METHOD AND APPARATUS FOR ANALYZING VOLATILE CHEMICAL COMPONENTS IN A LIQUID

[75] Inventor: Marsha L. Langhorst, Midland, Mich.

[73] Assignee: The Dow Chemical Company, Midland, Mich.

[21] Appl. No.: 641,992

[22] Filed: Jan. 16, 1991

Related U.S. Application Data

[63] Continuation-in-part of Ser. No. 236,069, Aug. 24, 1988, abandoned.

[51] Int. Cl.$^5$ .............................. G01N 7/00
[52] U.S. Cl. ......................... 73/19.02; 73/19.1; 73/19.12
[58] Field of Search ............... 73/23.35, 19.02, 19.12, 73/61.44, 864.81, 19.1; 55/53, 196, 197

[56] References Cited

U.S. PATENT DOCUMENTS

| | | | |
|---|---|---|---|
| 3,028,224 | 11/1962 | Ferrari | 23/232 |
| 3,065,148 | 11/1962 | Ferrari | 435/291 |
| 3,800,595 | 4/1974 | Vincent | 73/19.1 |
| 3,942,792 | 3/1976 | Topol | 73/19.1 |

FOREIGN PATENT DOCUMENTS 2079365 4/1987 Japan.

Primary Examiner—Jerry W. Myracle

[57] ABSTRACT

A sample of a volatile chemical component-containing liquid is segmented in stream flow with a gas with the volatile components partitioning or separating into the two phases, the gas then being separated from the stream and the volatile components therein analyzed for identification and concentration.

37 Claims, 8 Drawing Sheets

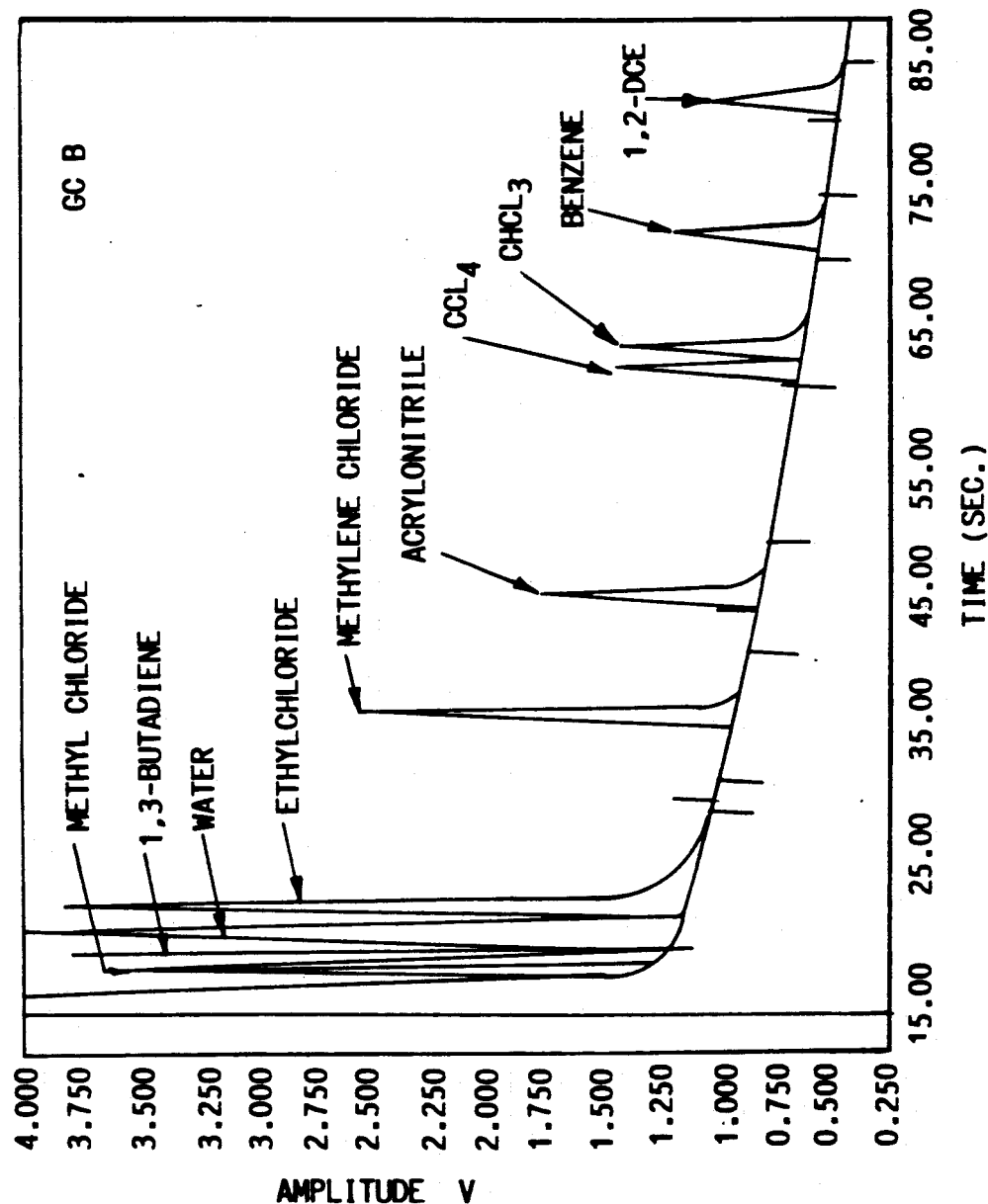

METHOD AND APPARATUS FOR ANALYZING VOLATILE CHEMICAL COMPONENTS IN A LIQUID

This is a continuation-in-part application of U.S. Ser. No. 236,069, filed Aug. 24, 1988, now abandoned.

TECHNICAL FIELD

The invention relates to improvements in methods and apparatus for the partitioning of volatile chemical components between liquid and gaseous phases with ultimate separation of the phases and analysis thereof.

BACKGROUND OF THE INVENTION

Various procedures have been developed to identify volatile components and concentrations thereof in a flowing stream. Such procedures include the combining of a liquid with a gas containing the components to be identified, inducing a reaction product, and separating such product through dialysis. It also has been proposed to react the resultant product to form a colored product to permit analysis thereof by means of a colorimeter. Additional procedures involve purge and trap analysis which is relatively slow and somewhat complicated. For example, purge and trap analysis frequently requires as much as 45 minutes to one hour to complete.

Head space analysis, although not being an on-line technique, is used extensively. This form of analysis is generally accomplished by partially filling a sealed vial with the liquid sample, placing the vial in a temperature controlled environment to permit the volatile components to come to equilibrium with the air or gas in the head space of the vial, and then sampling the head space gas and injecting the sample into a gas chromatograph to identify the volatile components and determine their concentrations.

Flow-through purge vessels combined with a gas chromatograph or hydrocarbon analyzer have been used for on-line analysis of volatile chemicals in water. In this technique, slow response to excursions is a major disadvantage and arises from the fact that the vessel acts as a dilution flask requiring a resulting high humidity stream to be taken continuously to the analyzer.

Still another procedure consists of a combined armored silicone hollow fiber and gas chromatograph for the analysis of volatile chemicals in aqueous solutions. Such a system can be used for trace environmental monitoring. Among the disadvantages of this type of system is that cryotrapping is required to reach low detection limits and the silicone fiber may accumulate higher boiling chemicals which are not readily swept away into the vapor stream.

The known procedures do not readily adapt themselves to on-line determination of the identity and concentration of volatile chemical components in water such as process aqueous streams, scrubber solutions, sewer legs to treatment plants, agricultural fumigant distribution systems, or the like because of complexity and excessive cycle time. There is a distinct need for an improved method and apparatus for determination of such volatile compounds and their concentrations, such method and apparatus being particularly adapted for use in environmental services, as in the testing of waste water and/or the determination of distribution of volatile soil fumigants in irrigation water.

SUMMARY OF THE INVENTION

In accordance with the present invention, there is provided a method of analyzing volatile compounds in a first fluid, the method including the steps of establishing a flowing stream of segments of the first fluid spaced by segments of other fluids, partitioning the volatile compounds into the other fluid segments from the first fluid segments, separating the other fluid segments from the first fluid segments, and analyzing the separated other segments to quantitatively analyze volatile compounds therein.

The present invention further provides an apparatus for analyzing volatile compounds in the first fluid, the apparatus including partitioning means for establishing a flowing stream composed of segments of the first fluid spaced by segments of the second fluid which partition the volatile compounds into the second fluid from the first fluid, separating means for separating the segments of the second fluid from the stream, and analyzing means for analyzing the separated segments of the second fluid to identify volatile compounds therein. Means are provided for delivery of the separated segments of the second fluid to the analyzing means.

FIGURES IN THE DRAWINGS

DETAILED DESCRIPTION

In a broad sense, the invention relates to a method and apparatus for forming a segmented flow stream of at least two fluids, partitioning volatile compounds from one segment to the other, separating the fluid segments and analyzing the separated fluid segments. The partitioning fluid is chosen so as to be able to remove the compounds from the other, as well as being easily handled for quantitation of the compounds therein. For example, if the compounds are in a water sample, the partitioning fluid can be a gas which has an ability to partition the compound from the liquid and can be analyzed by gas chromatography. In one embodiment, the system involves sampling water by means of a peristaltic pump and mixing the water with air to form the segmented air/water stream. The segmented stream is passed through a concentric hollow fiber unit, or the equivalent, where the segmented stream is debubbled. The water is then sent to waste, whereas the gas collected in the concentric hollow fiber unit is dehumidified and sampled for analysis by gas chromatography.

Figure 1:
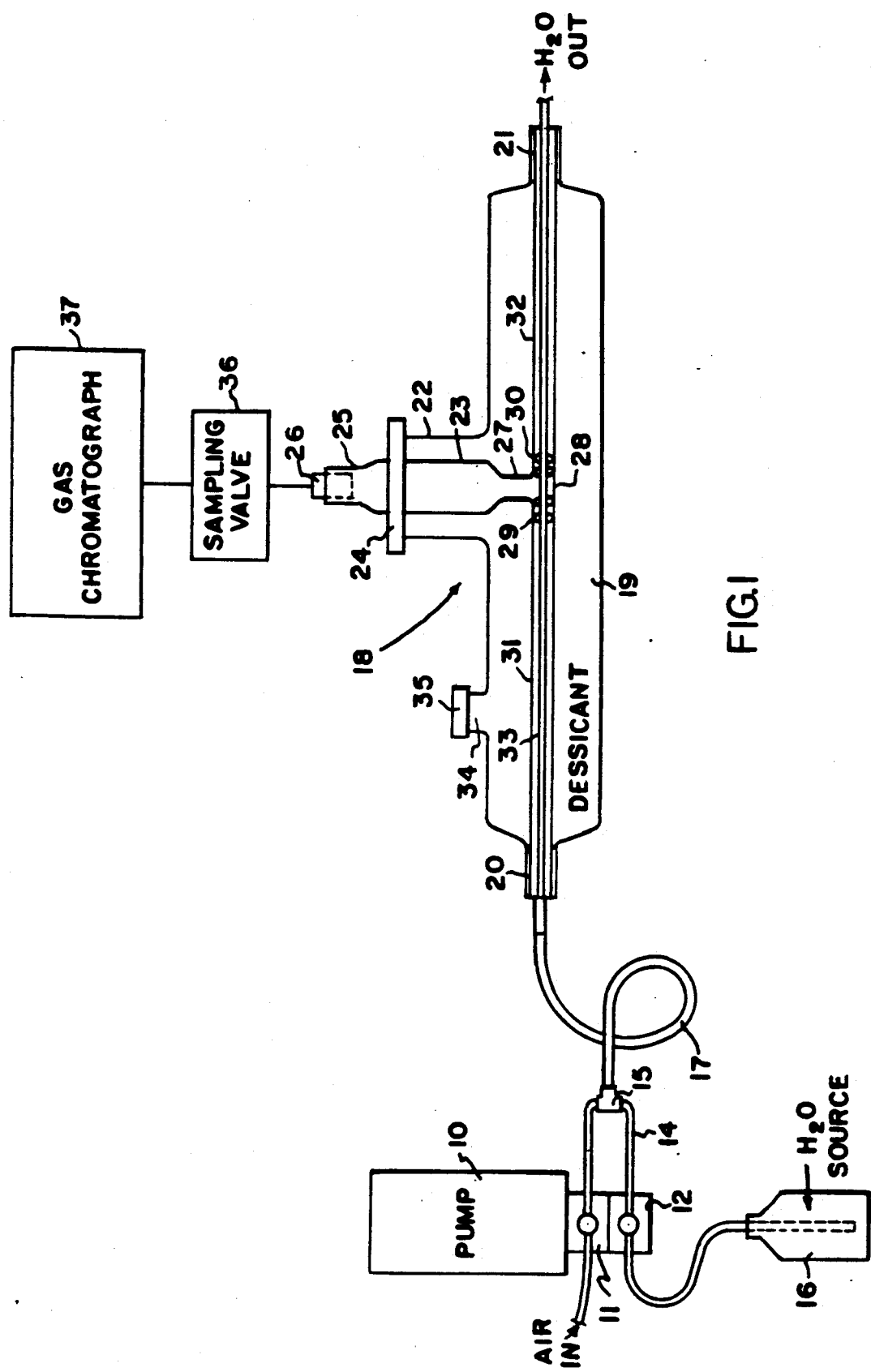
FIG. 1 is a schematic diagram of one form of apparatus suitable for use in practicing the subject invention.

FIG. 1 illustrates a preferred form of the apparatus wherein a peristaltic pump 10 having dual heads 11 and 12 is connected to an air supply line 13 and a liquid or water sample line 14. The pumping head 11 delivers air from any suitable source through line 13 to a connecting fitting 15, and the pumping head 12 delivers water from a source 16 through line 14 to connecting fitting 15. While the water source 16 is illustrated as a large bottle-type container with line 14 being submerged below the water level therein, any suitable source of liquid to be sampled may be utilized. For example, in an on-line application liquid supply line 14 may be connected to a pipe or other liquid conduit to obtain liquid samples directly therefrom.

Air supply line 13 may be connected to any suitable gas component source, such as air, nitrogen, or the like, the gas utilized being capable of combining with volatile compound compounds so as to act as a fluid medium in the operation of the system.

Fitting 15 produces a segmented stream in line 17 which is graphically illustrated as including a segmented stream flow consisting of alternating gas and liquid segments. The length of line 17 may be varied depending upon the equilibration time desired. Optimum length would be just long enough to allow equilibration. Minimal length better accommodates analysis of excursions.

During the flow portion of the segmented stream substantial transfer of compound components from the liquid segments to the gaseous segments occurs, the primary gradient or driving force accomplishing such transfer comprising the volatility of the compound components. For example, the apparatus functions effectively with volatile compound components exhibiting boiling points of up to approximately 180° C. Secondary gradients or driving forces exist, such as pumping pressure and sizing of stream flow lines. While equilibration is the theoretical goal, very substantial transfer will occur and such transfer very closely approaches equilibration. This type of transfer is also referred to as partitioning. Additionally, water vapor, which exhibits sufficient driving force, also will be transferred from the liquid segments to the gaseous segments and preferably subsequently removed.

The apparatus of FIG. 1 includes a concentric fiber transfer and dehumidifying unit 18 which may be made from any suitable material, such as glass. In a broad sense, unit 18 functions as a separation chamber and includes an elongated, generally cylindrical body 19 having opposite end neck portions 20 and 21, neck portion 20 being the inlet end of unit 18 and neck portion 21 defining one of the outlets of unit 18. Generally centrally of the unit 18, the body 19 is provided with an upstanding cylindrical column 22 within which is a generally concentric sampling column 23. Column 22 is sealed at its upper end by a removable cap 24 of any suitable kind which accommodates the upper end 25 of sampling column 23, such upper end defining a septum port 26 of known type. The base of sampling column 23 includes an area of reduce diameter 27 terminating at its lower end in a cylindrical foot portion 28 provided with oppositely directed, cylindrical, open ends 29 and 30.

Cylindrical end 29 receives telescopically therein the inner end of an outer cylindrical fiber segment 31, the outer end of which is sealed in neck portion 20. A second segment 32 of the outer cylindrical fiber segment 31 also has its inner end telescopically received in cylindrical end 30, its outer end being sealed in neck portion 21. An inner, continuous, cylindrical fiber 33 extends through neck portions 20 and 21, outer fiber segments 31 and 32, and cylindrical foot portion 28 of sampling column 23. One end of fiber 33 projects beyond neck portion 20 and is attached to segmented stream line 17, the opposite end of fiber 33 projecting outwardly of neck portion 21 for suitable attachment to a conduit or the like (not shown) to conduit water from the system and discharge it to waste. Unit 18 is completed with the provision of an access port 34 supplied with a removable cap 35 for the purpose of introducing and replacing desiccant in body 19 in substantially surrounding relation with outer cylindrical fiber segments 31 and 32.

Septum port 26 is preferably connected to any suitable type of sampling valve 36 which in turn is connected to a gas chromatograph 37 to complete the system.

The segmented air/water stream is delivered into and through inner continuous fiber 33 which is selected to permit transfer of gaseous material, including water vapor, therethrough thus functioning as a hydrophobic membrane. Gaseous material is collected within outer fiber segments 31 and 32 for sampling, and segments 31 and 32 are preferably selected to function as very selective hydrophilic membranes to permit transfer of water vapor into body 19 and into contact with the desiccant therein. In this manner, the volatile compound components of the original liquid stream are isolated for analysis and simultaneously dehumidified.

Sampling valve 36 is operated periodically to withdraw air enriched with compound components from column 23 which, in turn, is in communication with the interior of outer fiber segments 31 and 32 via foot portion 28. Each sample taken is transmitted to a known type of gas chromatograph 37 which analyzes each sample to identify and determine the concentration of the compound component content thereof.

The apparatus described thus far is capable of on-line utilization. It also is adapted for use as a portable field testing system. For example, sampling valve 36 may be replaced in the field with a suitable probe or gas-tight syringe for use in conjunction with septum port 26 to obtain periodic samples for introduction into a portable gas chromatograph.

Transfer unit 18 may include the use of a microporous polytetrafluoroethylene (TFE) tubing as its inner continuous fiber 33. While any suitable type of hydrophobic microporous membrane, such as polypropylene, may be used, in the following examples the TFE fiber tube 33 is incorporated in the test equipment and is commercially identified as GORE-TEX by its manufacturer, Gore, Inc. The tube has an inner diameter of 1 mm., 3.5 micromillimeter pores, and 70% porosity. This material is hydrophobic and compoundly inert. Its hydrophobicity, along with the high surface tension of water, creates a phenomenon whereby air and vapors can pass through the fiber's pores while aqueous solutions remain in the fiber bore.

The use of outer fiber segments 31 and 32 is not essential, but some effective form of dehumidification is desirable. The fiber used to form these segments may be a perfluorosulfonic acid product, such as that sold under the DuPont trademark NAFION. The fiber segments were formed from 810X tubing having an inner diameter of approximately 2.75 mm. and an outer diameter of approximately 3.125 mm. This perfluorosulfonic acid product provides a membrane with a high capacity and high selectivity for water vapor. It is also inert to volatile, halogenated compounds.

The desiccant used to fill body 19 of unit 18 was standard indicating silica gel.

Any suitable type of pump 10, such as the FMI Lab-Pump Jr., may also be used.

Tests conducted using the apparatus thus far described included the use of either a portable micro-gas chromatograph equipped with a u-thermal conductivity detector or a standard type laboratory gas chromatograph equipped with an electron capture detector. A suitable microchip gas chromatography unit for field use is a Model M500 or P200D analyzer obtainable from Microsensor Technology, Inc., Freemont, California. A conventional laboratory style chromatograph may be a Model 5890 obtainable from Hewlett-Packard, Novi, Michigan. The column used with such a unit may have a length of 15 m. to 30 m. with an internal diameter of 0.1 mm to 0.53 mm. DURA-BOND coating 1301 as well as others with a thickness of 0.4 to 5 microns may be used. Such a column and coating are available from J & W Scientific, Folsom, California.

To illustrate the feasibility of monitoring the distribution of volatile solid fumigants in irrigation water, a water sample containing 100 micro-grams per milliliter, of TELONE C-17 (a trademark of Dow Chemical Co., Midland, Michigan), was formed into a segmented stream in the manner previously described in connection with the apparatus of FIG. 1. This TELONE C-17 sample contained approximately 40 μg/ml t-1,3-dichloropropene, 35 μg/ml c-1,3-dichloropropene, and 17 μg/ml chloropicrin. The water sample was placed in container 16, pumped through line 14, and combined with air at fitting 15. The segmented stream was passed through inner fiber 33 and the air phase, now containing the volatile compound constituents, was transferred through the membrane defined by fiber 33 along with water vapor into the annular space surrounding inner fiber 33 and confined within outer fiber segments 31 and 32. During movement through unit 18 by pump 10, the selective hydrophilic properties of outer membrane segments 31 and 32 transferred water vapor into contact with the desiccant within body 19 while selectively retaining the remaining air and compounds mixture, such mixture ultimately filling sampling column 23 and being available for sampling through septum port 26.

Instead of using the sampling valve 36, a known sampling probe forming a part of a micro gas-chromatograph of the type previously described was used to transfer a sample of approximately 5 ml. of the gaseous mixture to the chromatograph where small micron-liter portions of the gas was injected into the 0.1 mm. internal diameter capillary columns for analysis. The gas sample was analyzed on one or more of the internal miniaturized gas chromatograph modules, simultaneously. This type of instrument was used to analyze over 120 different compounds (gases/vapors) with typical analysis times in less than 60 seconds. Such a chromatograph may be operated in an automated sampling mode, automatically sampling and analyzing the vapors at pre-selected sampling intervals and storing the results for subsequent recall. Such a microgas chromatograph utilizes miniaturized thermal conductivity detectors with high sensitivity.

The chromatographic columns used with the micro gas-chromatograph were 0.3 to 4 m. long, and of 0.1 mm. inner diameter. The capillary columns were coated with DURA-BOND 1701 phase at a thickness of 0.1 to 0.5 microns. The carrier gas utilized in the chromatograph was helium traveling at approximately 100 cm/sec.

The results of the TELONE C-17 analysis are shown in FIG. 5 in the form of a chromatogram combined with a list of compounds and concentrations thereof identified by the chromatogram. In the typical chromatogram shown in FIG. 5, the ordinate denotes quantitative detection and the abscissa measures time of detection, or as is more commonly referred to, time of retention. Time of retention or identification of the constituents of the tricompound material took no more than a total of seven seconds and quantitative detection accurately confirmed known concentrations of the compound constituents.

Additional tests were conducted not only to confirm the quantitative accuracy of the subject method and apparatus, but also to explore the speed of detection response in more complex systems. Such tests involved use of different combinations of volatile compounds in varying numbers and concentrations in water, the concentrations ranging from 4 to 1000 ng/ml. A typical test involved a water sample containing 24 volatile halogenated compounds, the results of which are shown in FIG. 6 consisting of a chromatogram combined with a list of the compound compounds detected, their respective concentrations and retention times. In tests such as that of FIG. 6, the laboratory gas chromatograph described above was utilized. Samples in quantities of 1 ml. were withdrawn from the apparatus of FIG. 1 through septum port 26 using a sampling probe.

The test results of FIG. 6 further illustrate the speed of detection of the subject method and apparatus thus permitting effective use thereof in a rather complex compound system. Of particular importance, the method and apparatus exhibit the desirable capability to detect concentrations including temporary excursions.

The various tests conducted established that certain standards can be determined for each volatile compound compound of the type reasonably expected to be encountered in environmental monitoring of waste water, irrigation water and the like. It has been found that the detection sensitivity of the subject method and apparatus for an array of volatile compound compounds can be expressed in the form of enrichment factors with a single such factor being unchangeably assignable to each compound compound subject to detection. That is, each enrichment factor is a direct measure of the detection capabilities of the method and apparatus with respect to a specific volatile compound compound. The following table illustrates this discovery with respect to 22 volatile compound compounds:

TABLE

| COMPOUND | LOD in air (ppb - v/v) | EF (air/ water | LOQ in water (ng/ml) |
|---|---|---|---|
| METHYL CHLORIDE | 330 | 48 | 23 |
| METHYL BROMIDE[(a)] | 137 | 76 | 6.0 |
| VINYLIDENE CHLORIDE | 6.8 | 12 | 1.9 |
| METHYLENE CHLORIDE | 22 | 8.2 | 9.2 |
| t-1,2-DICHLOROETHYLENE | 200 | 16 | 42 |
| 1,1-DICHLOROETHANE | 270 | 6.7 | 130 |
| CHLOROFORM[(b)] | 2.7 | 6.6 | 1.4 |
| 1,1,-TRICHLOROETHANE | 2.5 | 6.8 | 1.2 |
| CARBON TETRACHLORIDE | 0.54 | 7.7 | 0.23 |
| 1,2-DICHLOROETHANE | 76 | 6.8 | 37 |
| TRICHLOROETHYLENE | 2.8 | 9.9 | 0.94 |

TABLE-continued

| COMPOUND | LOD in air (ppb - v/v) | EF (air/ water) | LOQ in water (ng/ml) |
|---|---|---|---|
| 1,2-DICHLOROPROPANE | 120 | 7.7 | 54 |
| BROMODICHLOROMETHANE | 3.0 | 7.7 | 1.2 |
| t-1,3-DICHLOROPROPENE | 26 | 7.2 | 12 |
| c-1,3 DICHLOROPROPENE | 30 | 3.6 | 28 |
| 1,1,2-TRICHLOROETHANE | 15 | 3.9 | 13 |
| PERCHLOROETHYLENE | 0.69 | 4.8 | 0.48 |
| CHLORODIBROMOMETHANE | 4.6 | 3.7 | 4.2 |
| CHLOROBENZENE | 310 | 4.0 | 260 |
| BROMOFORM | 9.4 | 2.0 | 16 |
| 1,1,2,2-TETRACHLOROETHANE | 10 | 2.0 | 17 |
| 1,2-DICHLOROBENZENE | 90 | 1.7 | 170 |

(a)ETHYL CHLORIDE is not included because it co-elutes with METHYL BROMIDE
(b)BROMOCHLOROMETHANE co-elutes with CHLOROFORM.

The foregoing table includes for each compound listed a measured detection limit in air (LOD), an extrapolated quantitation limit in water (LOQ), and a calculated enrichment factor (EF). Both the detection limit in air and quantitation limit in water will vary depending on the sensitivity of the analytical equipment used. Thus, at any given testing site the sensitivity of the particular gas chromatograph used will determine detection and quantitation limits.

By way of example, the results of the subject tests listed in the foregoing table involved the use of the laboratory gas chromatograph identified above. With such an instrument, the LOD values are measurable at three times the signal-to-noise ratio. Since the actual analysis of the volatile compounds in the water samples involves measurement in the vapor phase, the LOD values establish the limits of sensitivity or detection for the instrument.

Without benefit of known enrichment factor for each compound compound present, extrapolation of the quantitation limit (LOQ) for each compound was accomplished by multiplying the signal-to-noise ratio of the test instrument by ten. These quantitation limits are a reflection of both the detector sensitivity (LOD) and what can be referred to as the enrichment factor or magnification of the concentration into the air phase. Thus, an enrichment factor was calculated for each compound as follows:

$$EF = \frac{\text{con. in air (ppb} - \text{v/v)}}{\text{conc. in water (ng/ml)}}$$

The enrichment factor depends on the volatility, water solubility, and diffusion coefficient of the particular compound. This factor has been, established to illustrate the measurement sensitivity of the compound which is usually enhanced by the use of the method and apparatus of the subject invention. Once the enrichment factor is determined for a given compound, a helpful constant which is independent of the type of detector used is provided to determine quickly and accurately quantitation limits in a water sample using the foregoing equation modified as follows:

$$LOQ \text{ (ng/ml)} = \frac{LOD \times 3.33}{EF}$$

Enrichment factors may be relied upon to establish a range useful in identifying volatile compound compounds subject to detection and quantitation in a fluid medium such as water. The table set forth above establishes a range from 1.7 to 76 while interpretation of additional test results and consideration of properties of known compounds establishes a practical range of from 1 to 100. The more volatile and less water soluble compounds exhibit the higher enrichment factors.

It has been found that equilibration for an upward change in concentration can be 90 to 100 per cent complete in approximately 10 to 15 minutes. This means that a shot or excursion concentration could be detected on the very next analysis. Cycle time with the laboratory gas chromatograph has been found to average approximately 12 minutes. This is a substantial improvement as compared to conventional purge and trap analysis which can require as much as 45 minutes to one hour per cycle.

It has been found that the method and apparatus of the present invention permit full utilization of a wide range of concentrations of compounds, from low values in sub-parts per billion to substantial values in high parts per million. No supplemental sorbent trapping is necessary.

The use of concentric hollow fibers in the manner described provides for increased component transfer area in a minimum of space. The primary driving force or gradient comprises essentially the volatility of the compound compounds in the waste water causing ready enrichment of the air segments. Transfer is also assisted by pressurized flow provided by pump 10. The water, in effect, is debubbled. The desiccant located externally of fiber segments 31 and 32 provides a gradient or driving force assisting in transfer of water vapor through the membranes provided by the fibers.

The precision deviation for repetitive analyses in water has been found to range from about 0.35% to 17%, averaging approximately 6.5%. Based on extensive evaluation, it has been established that the subject invention consistently requires less than 15 minutes per analysis.

While the type of concentric hollow fiber unit described is preferred, the outer tube segments 31 and 32 may be eliminated, although dehumidification in some suitable manner preferably should occur inasmuch as temperature changes can cause condensation to occur which can slow the process. Thus, dehumidification speeds transfer and efficiency of transfer in a direction toward equilibration.

When utilizing membrane segments 31 and 32 for removal of water vapor from the air/compounds mixture, a concentration radient may be established by continuously purging the interior of body 19 with dry air, thus eliminating the need for a desiccant.

Figure 2:
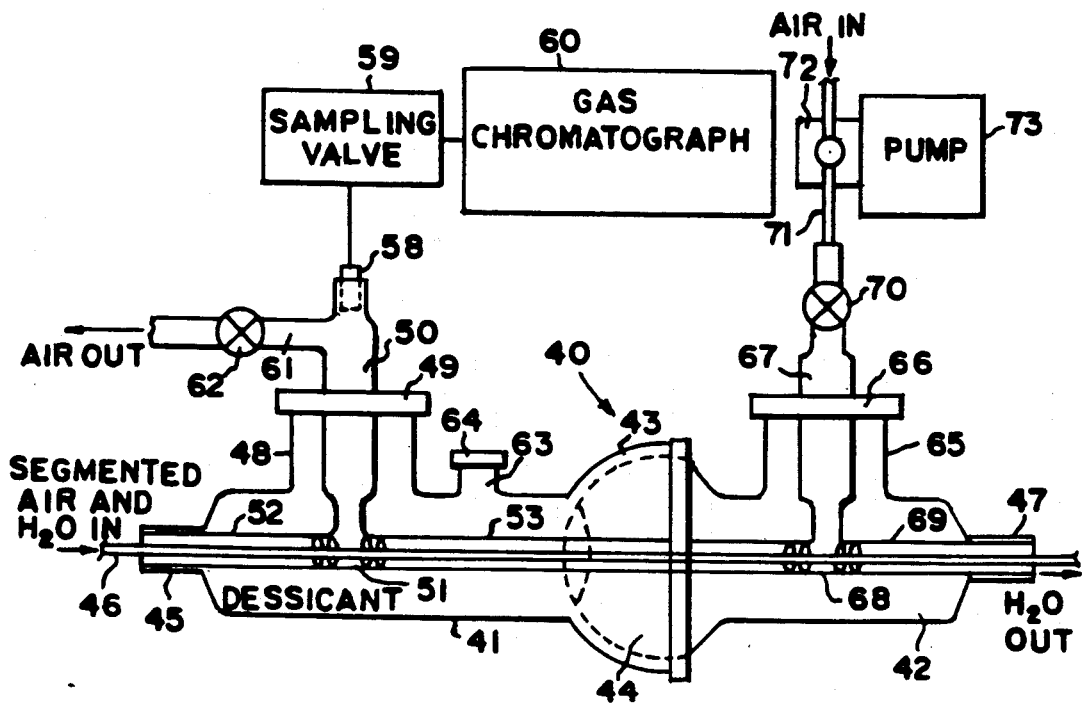
FIG. 2 is a schematic diagram of a modified form of the apparatus.
Figure 3:
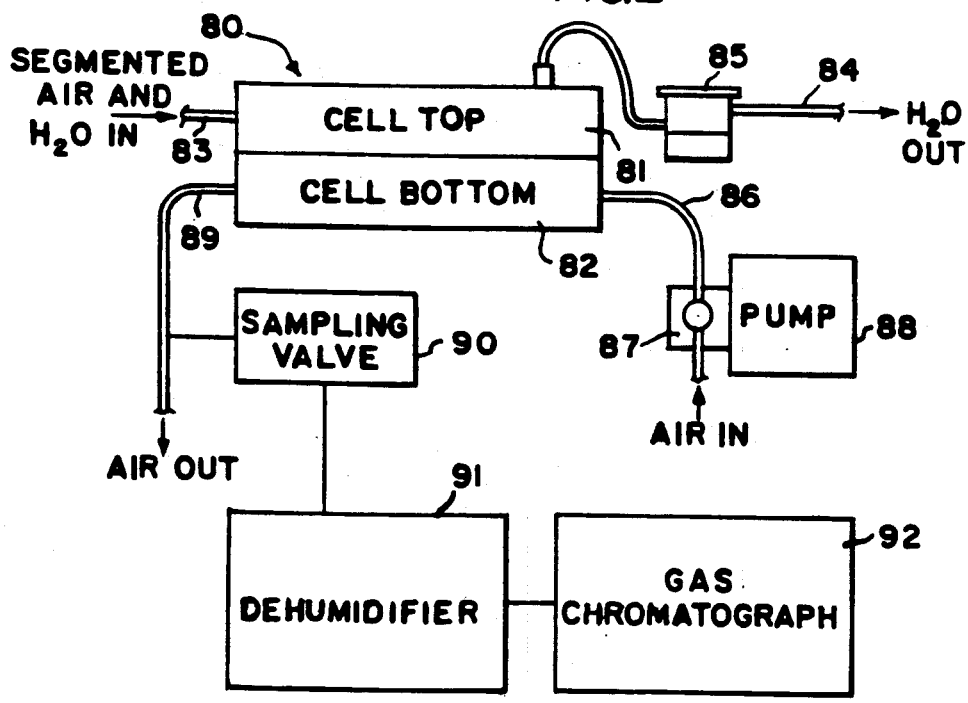
FIG. 3 is a schematic diagram of still another modified form of apparatus.
Figure 5:
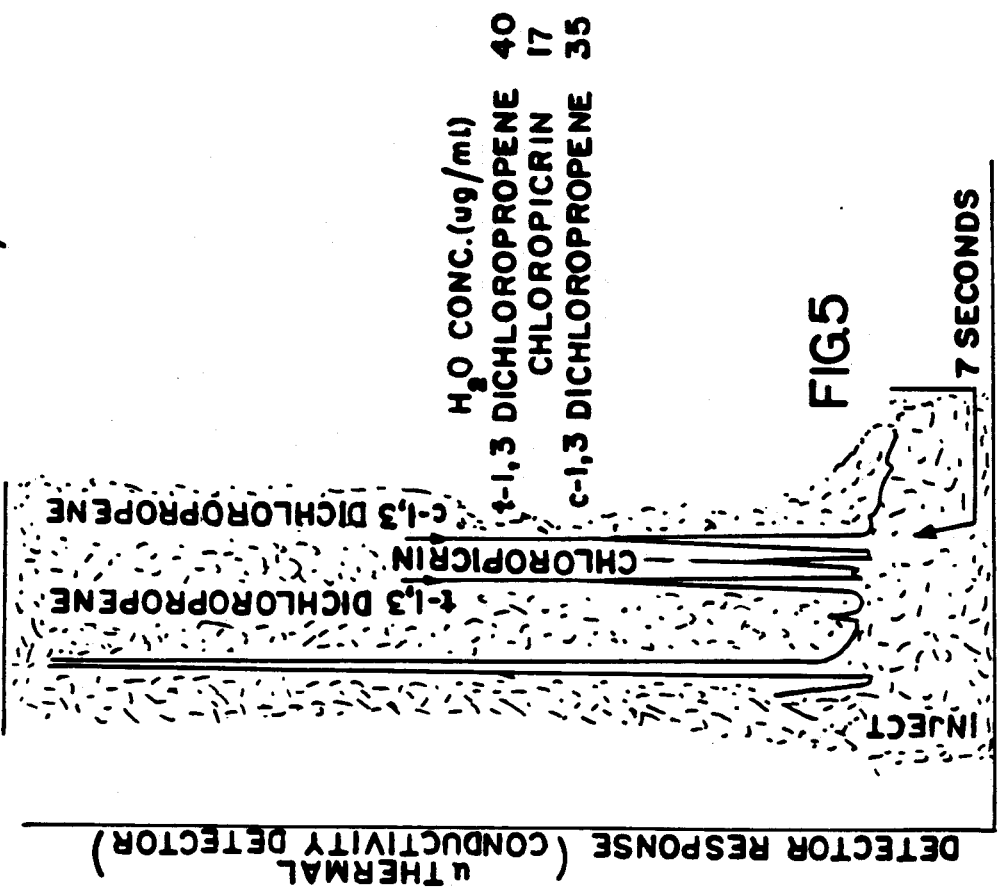
FIG. 5 is a chromatogram graph of a sample analysis performed in accordance with the present invention.
Figure 4:
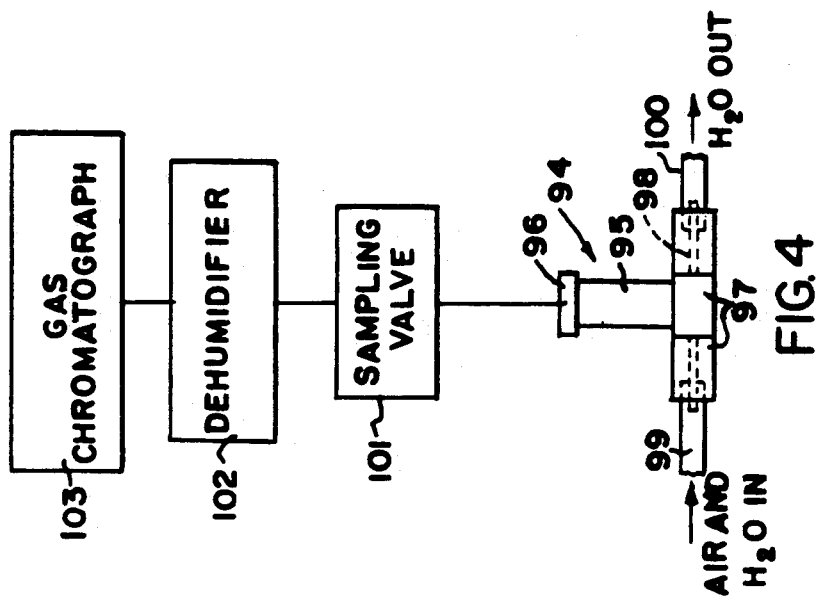
FIG. 4 is a schematic diagram of a simplified form of the apparatus.
Figure 6:
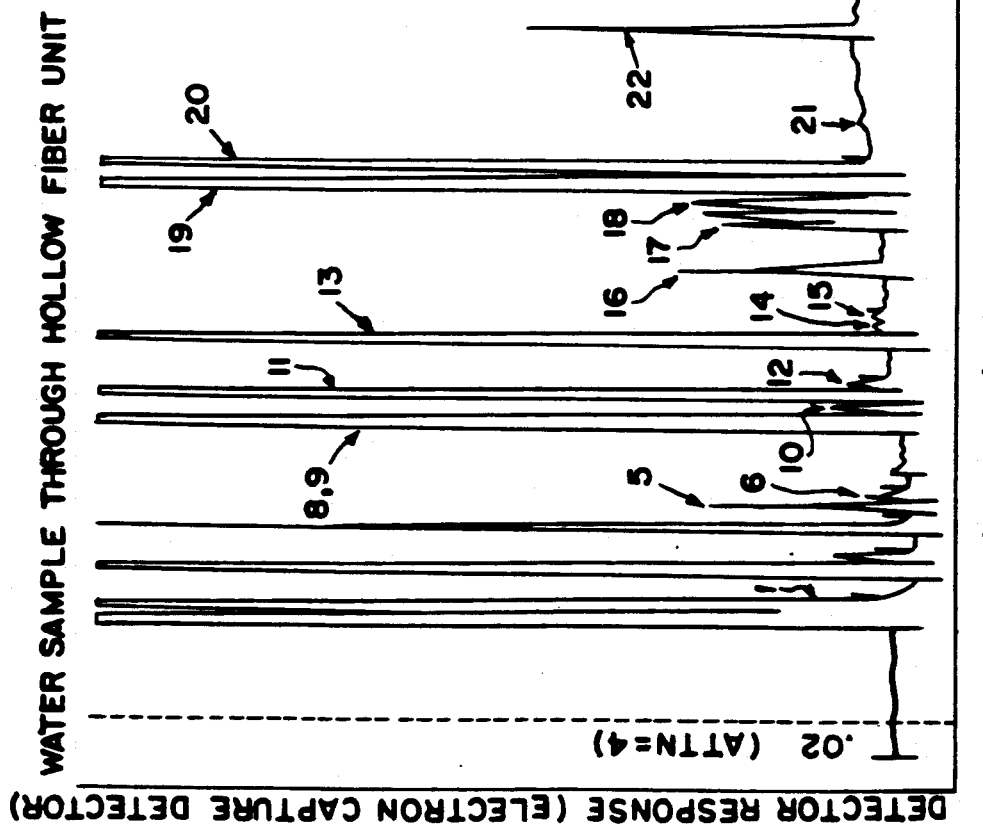
FIG. 6 is another chromatogram graph of a more complex and lower concentration analysis performed in accordance with the present invention.

The versatility of the present invention is further illustrated in the embodiments of FIG. 2-4. FIG. 2 discloses a portion of a modified system including in particular a modified gas transfer unit 40. For ease of construction this unit includes a glass body formed from a pair of cooperating body portions 41 and 42, portion 41 including a socket 43 within which is a cooperating ball 44. Body portion 41 is provided with a closed neck end 45 through which extends an inner hollow fiber 46 through which a segmented stream of air/water may flow into unit 40 in the same manner as shown in FIG. 1. Hollow fiber 46 extends through the combined body portions 41 and 42 and outwardly beyond a closed neck end 47 at the opposite end of body portion 42 in communication with a suitable water disposal system (not shown). Body portion 41 includes an upstanding cylindrical column 48 provided with a removable closure 49 through which a cylindrical, upwardly extending gas sampling column 50 extends Column 50 is provided with a bottom transverse foot portion 51 receiving in telescoped relation in opposite ends thereof segments 52 and 53 of an outer hollow fiber, the remaining end of segment 52 being fixed in closed neck end 45. This telescopic arrangement is similar to that disclosed in FIG. 1. Column 50 includes at the top thereof a septum port 58 connected to a sampling valve 59 which in turn is connected to a known form of gas chromatograph 60. Column 50 further includes a transversely extending gas flow line 61 equipped with a stopcock 62 operable selectively to release air/compounds previously sampled into a suitable disposal system (not shown). Body portion 41 is further provided with an access port 63 provided with a removable cap 64 to enable the supply and removal or replacement of desiccant surrounding fiber segments 52 and 53.

Body portion 42 is similarly provided with an upstanding cylindrical column 65 having a removable closure 66 through which an upstanding cylindrical column 67 extends. The inner bottom of column 67 is provided with a transverse foot portion 68 of the type previously described which telescopingly receives adjacent ends of outer fiber segments 53 and 69. The remaining end of segment 69 is sealed in closed neck end 47. Inner hollow fiber 46 extends continuously through the outer hollow fiber segments 52, 53 and 69 as well as through the foot portions 51 and 68. The top outer portion of cylindrical column 67 projecting above closure 66 is provided with a stopcock 70 (diagrammatically shown) and beyond such stopcock communicates with an air supply line 71 which extends through the single head 72 of a peristaltic pump 73.

The apparatus of FIG. 2 is illustrative of one form of flow-through purging system. Such a system is of significance in on-line operation particularly where excursions are expected and are to be detected.

As referred to hereinabove, substantial equilibration for an upward change in concentration has been found to be 90 to 100% complete in approximately 10 to 15 minutes for all of the compounds tested. With this rate of reaction efficiency, a shot or excursion concentration should be detected as it occurs. However, in some instances recovery to zero after a concentration excursion can be relatively slow, even as long as 60 minutes. This is because dead volume exists inside the concentric hollow fiber unit. This, combined with a withdrawal of a small sample, e.g. 1 ml, for analysis, tends to cause stagnation thereby requiring a substantial amount of time to clear out the system for subsequent effective operation.

In the apparatus of FIG. 2, pump 73 on demand supplies air to the interior of the outer hollow fiber segments, especially segment 53, such air forcibly clearing out any stagnant gases through column 50 past stopcock 62. This allows rapid downward recovery in concentration as well as upwardly increased detection of excursions. Thus, even for a 7 second analysis of the type previously described, the stopcocks 62 and 70 may be operated quickly and effectively to purge the system prior to further sampling. The concentric fibers disclosed in FIG. 2 are of the same type as referred to in connection with FIG. 1 and operate in the same manner.

FIG. 3 illustrates another form of equilibration apparatus including a stainless steel membrane cell 80 subdivided into a top cell 81 and a bottom cell 82 separated by a transverse membrane (not shown) which may be formed from microporous polypropylene film. Top cell 81 includes an inlet 83 for segmented air and water of the nature described previously, and a water outlet 84 connected to waste or the like after passing through a back pressure valve 85 of known type. Bottom cell 82 is provided with an air inlet line 86 which passes through the single head 87 of a peristaltic pump 88. Bottom cell 82 also includes an air outlet line 89 that is connected to a sampling valve 90 which in turn is connected to a dehumidifier 91 and a gas chromatograph 92. Membrane cell 80 may be a modified Amicon CECl on-line column eluate concentrator available from Amicon Corporation, Lexington, Massachusetts.

It is also is possible to use a microporous membrane between the upper and lower cells such as that formed from CELGARD 2400 (trademark of Celanese Corporation, Charlotte, North Carolina) microporous polypropylene film. Such a film is about 38% porous and has a thickness of 1 mil.

The system of FIG. 3 provides a continuous flow of a segmented air/water stream through top cell 81 across the membrane separating top cell 81 from bottom cell 82, while additionally providing a continuous flow of air through bottom cell 82. The membrane selectively transfers the air segments containing the volatile compounds as well as water vapor, such transferred components being picked up by the continuous air flow through bottom cell 82 with periodic samples being taken therefrom via sampling valve 90, the samples being dehumidified to remove water vapor and then subjected to analysis in gas chromatograph 92. In a continuous flow-through system of this type or a stop flow system, stagnation is avoided, excursions are readily determined, and the speed of analysis is high.

FIG. 4 illustrates a simplified form of a sampling system further illustrating the versatility of the present invention. The system of FIG. 4 includes a solvent debubbler 94 which is in the form of a translucent reservoir 95 provided with an airtight cap 96. The debubbler 94 may be obtained from Anspec Co. and has been used to remove bubbles from the pump inlet line of a high pressure liquid component system. Debubbler 94 includes a base 97 receiving therein a section of hollow fiber 98 prepared from microporous TFE of the type previously described. One end of fiber 98 is attached to a segmented air/water sample supply line 99 and the opposite end is attached to a waste water line 100. Fiber 98 is in communication with reservoir 95.

A segmented stream of the type previously described is supplied via line 99 through hollow fiber 98. In base 97 of debubbler 94, air mixed with volatile compounds transfers through fiber 98 into reservoir 95. A suitable form of sampling valve 101 may be attached to debubbler 94 through cap 96 to receive periodic samples with each being transferred to dehumidifier 102 and then for analysis to gas chromatograph 103. Thus, a very basic, uncomplicated, and inexpensive volatile compounds transfer system may be fabricated. As previously described, the use of a dehumidifier in the systems of FIGS. 3 and 4 is not essential, but is preferred.

Figure 7:
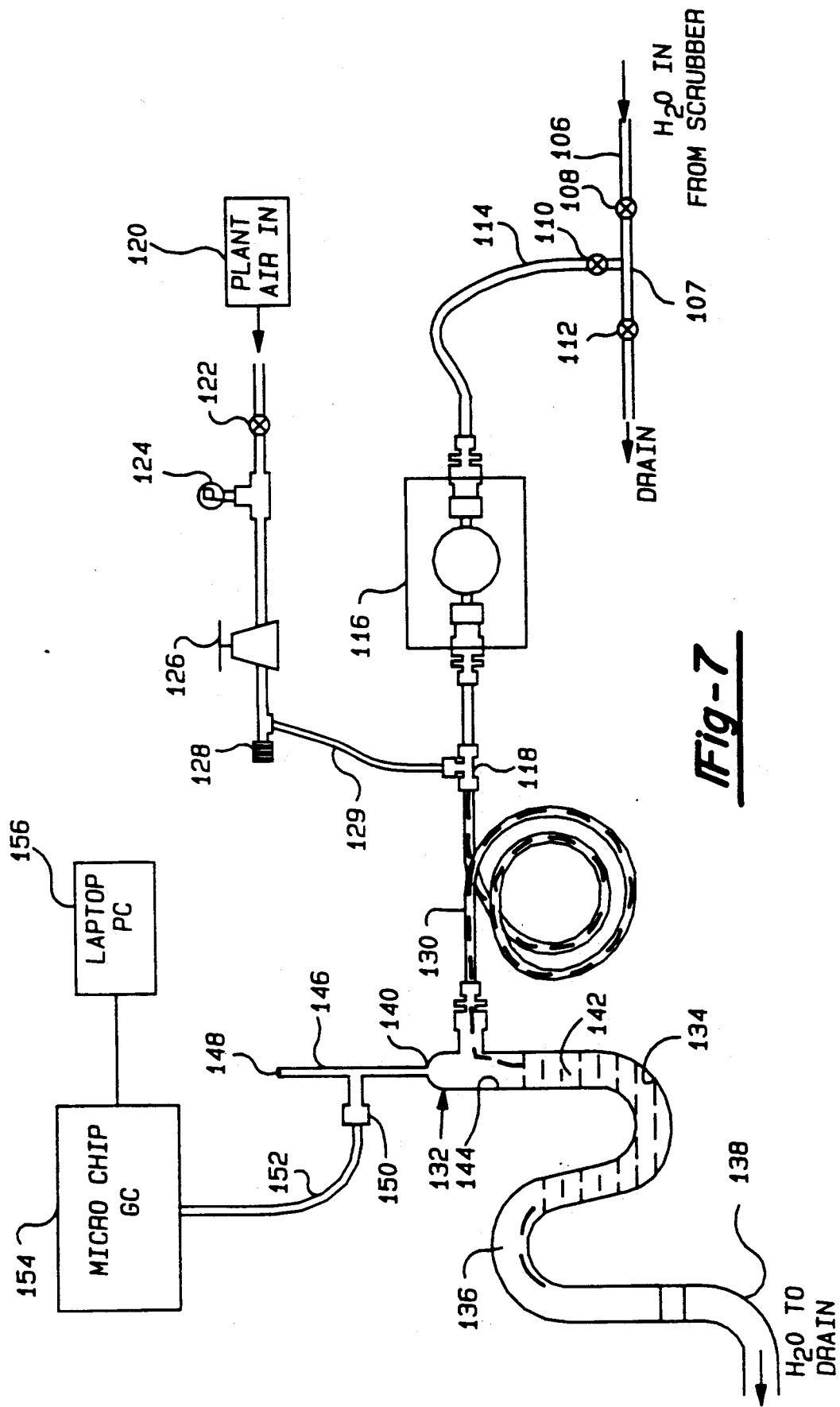
FIG. 7 is a schematic diagram of another form of apparatus suitable for use in practicing the subject invention.
Figure 8:
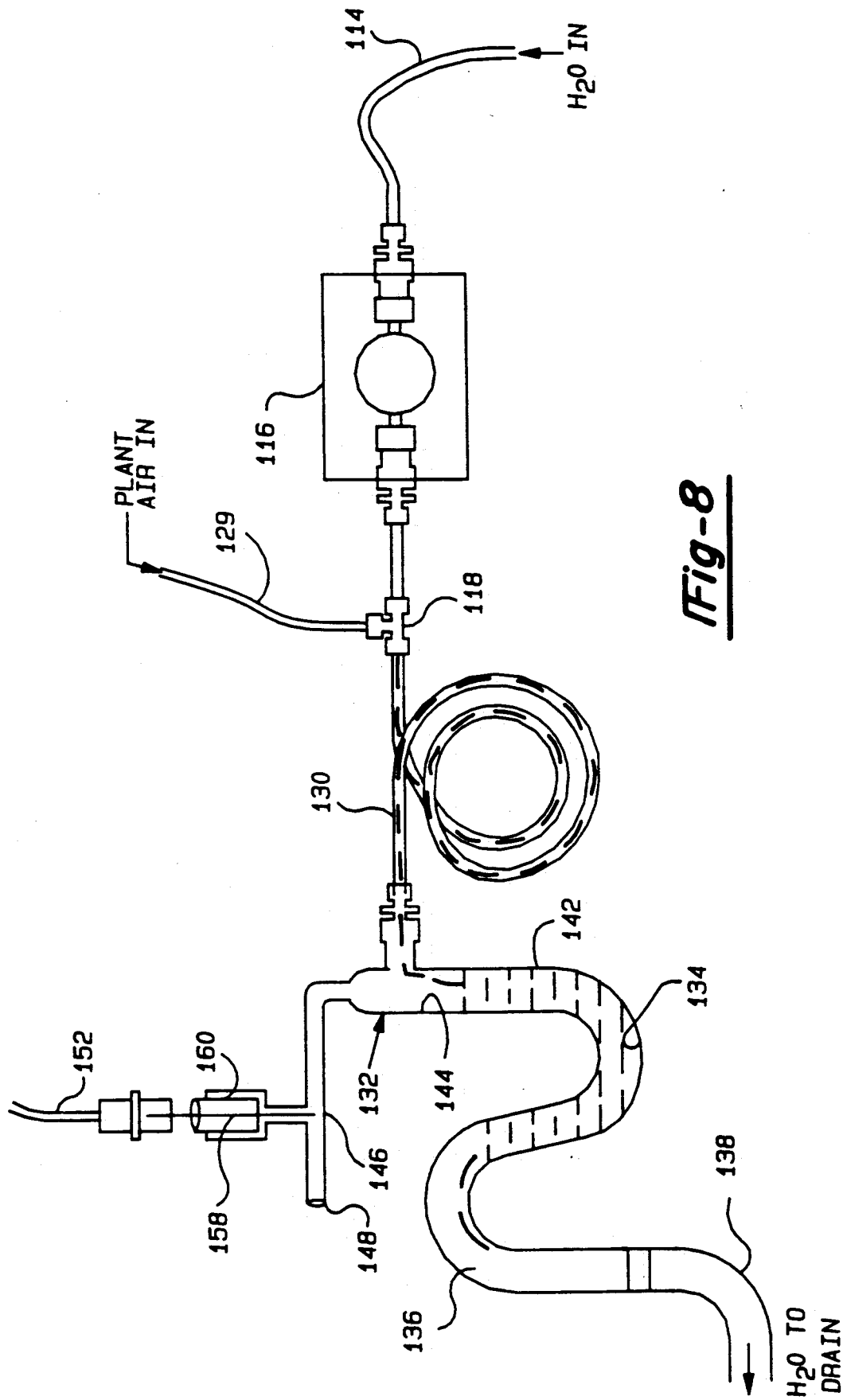
FIG. 8 is an enlarged schematic diagram of the sampling system of the apparatus of FIG. 7.
Figure 9A:
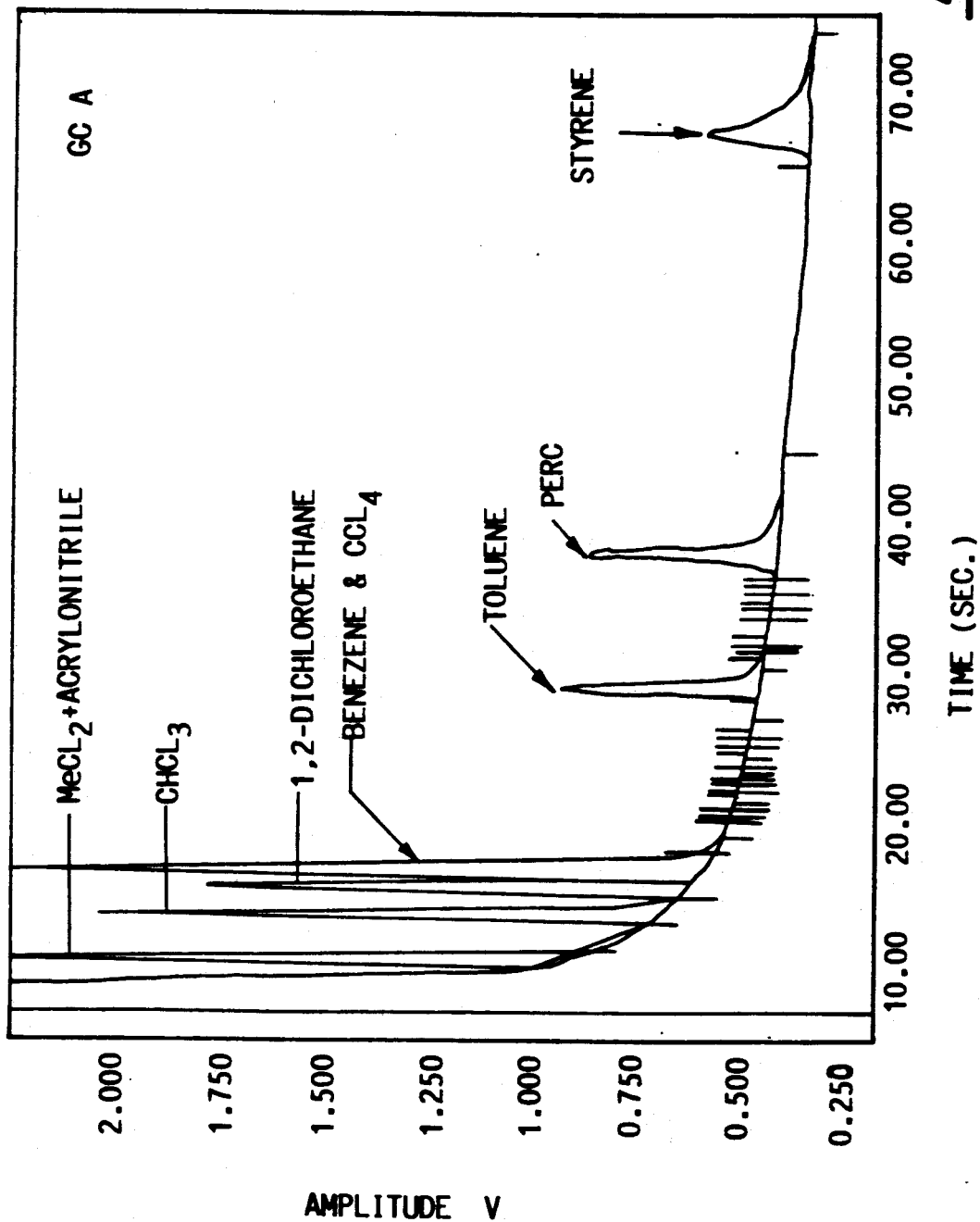
FIG. 9(A and B) shows two chromatogram graphs of sample analysis performed in accordance with the present invention.

Another, simplified embodiment of the present invention is shown in FIGS. 7 and 8. Tubing 106, such as ¼ inch Teflon tubing leads from a scrubber and carries water therein. The tubing 106 includes a T-portion 107, the flow therethrough being controlled by valves 108,110,112. Valves 108 and 112 control the flow of water through tubing 106 to a drain (not shown) while valve 110 controls the flow of fluid to tube 114 which leads to the fluid pump 116. In the preferred embodiment, FMI lab pump Jr., model RHSYOCKC, was used. The pump 116 pumps the fluid from tubing 106 to the T member 118. This member 118 can be a ⅛ inch Teflon T disposed down stream of the pump 116. An air source 120 is connected through valve 122 and pressure gage 124 to a Watts regulator 126 which controls flow to a needle valve 128. The needle valve 128 is in fluid communication through tubing 129 to the Teflon T 118. Tubing 129 can be in the form of a ⅛ inch Teflon tube. Of course, the sizes of tubing depend upon volumes and rate of fluid being moved therethrough. The Teflon T 118 is in fluid communication with the air source and the water being supplied from the scrubber. The two are fed together through the Teflon T 118. The air may be fed into the system from plant air or from other sources as previously described. As discussed with previous embodiments, the Teflon T 118 produces a segmented stream in line 130. The length of line 130 may be varied depending upon the equilibration time desired. Optimum length would be sufficiently long so as to allow equilibration. Minimal length better accommodates analysis of the excursions.

The air/water segments flow through line 130 into the glass phase separator generally indicated at 132 and shown in greater detail in FIG. 8. While the air/water segments are flowing to the glass phase separator, the volatile compounds in the water partition into the air and reach equilibration concentrations dependent upon the length of line 130, as discussed above.

The glass phase separator 132 is a substantially S-shaped member including a water drain trap portion 134. The water drain trap portion 134 leads to an overflow drain portion 136, the drain portion 136 leading to piping 138. Piping 138 carries overflow water to a drain (not shown). The separator 132 includes a gas outlet 140.

As shown in FIGS. 7 and 8, water 142 is allowed to collect in the trap portion 134 and then drain through the overflow portion 136 into drain pipe 138. Coincidently, the vapors of the volatiles that have been separated collect in a small head space volume 144 above the water 142. The vapors in the head space 144 exit the outlet 140 into a neck portion 146 having an air outlet 148. The outlet 148 is necessary because of the flow of water into the system causing a slight positive pressure of air exiting the glass phase separator 132. This slight positive pressure allows for real time analysis of the concentrations of the volatile compounds in the water as the positive pressure continues to displace the volume in the head space 144 which is being sampled. That is, the positive pressure is continually forcing newly separated volatiles into the head space 144 which then travels through the neck portion 146. Sampling is conducted in the neck portion 146, the gas not being sampled exiting the neck portion through outlet 148.

A needle valve 150 and tubing 152 interconnect the neck portion 146 in fluid communication with a microchip gas chromatograph 154 and lap top personal computer 156. The tubing 152 can be a 1/16 inch tubing. The needle valve 150 consists of a needle 158 and septum 160, the needle being disposed through the septum 160 and into the neck portion 146. The tubing 152 is connected through an adaptor to a needle 158.

The microgas chromatography system is preferably a Michromonitor P-200 which is a compact, portable unit containing two miniaturized gas chromatography modules, an internal sampling pump, a lead-acid battery, and an internal, rechargeable carrier gas supply. The gas chromatograph modules, constructed using silicon micro machining techniques, incorporate a solid state injection system, a short, high speed analytical column, a column heater and temperature sensor, and a 20 nL volume thermal conductivity detector. This system is preferred because it is capable of very high separating efficiencies with typically 10 to 45 second analysis time. When the P-200 is used with a lap top computer and EZCHROM software package, the system forms an automated, flexible gas/vapor analysis and data logging system. Of course, other microchip gas chromatograph systems could be designed and used in accordance with the present invention. The system described above can be configured for use in a wide variety of applications for the determination of over 200 gases and vapors. The instrument is suitable for measuring concentrations from one part per million - v/v to 100%, with linear response over five orders of magnitudes. The concentrations measured in the vapors are related to the concentrations of the components in the water, based on partition ratios, which were determined based on lab analysis of water standards and samples at 21° to 22° C. For field use, a portable, air purged, temperature-controlled box is used.

In operation, a vapor sample is drawn into the instrument through the 1/16 inch tube 152 or sampling probe with an integral sampling pump and, then, simultaneously injected into the two GC modules for analysis with the optimum resolution and speed. The chromatograms are processed using the external lap top microcomputer, calculating the concentration results within internally stored response factors.

The system was evaluated initially by being set up for the determination of twelve compound compounds, and separating the compounds of interest in 90 seconds. The test compounds included: methyl chloride, 1,3-butadiene, ethyl chloride, methylene chloride, acrylonitrile, carbon tetrachloride, chloroform, benzene, 1,2-dichloroethane, toluene, tetrachloroethylene, and styrene.

The present invention is especially useful for in situ monitoring of process vapors for environmental waste reduction projects, material balance investigations, and evaluation of emission control equipment. With typical analysis times of between 10 and 45 seconds, the system has already been useful for generating time-concentration profiles on batch-operated processes. When coupled with flow data-logging, detailed emission rate profiles or material balance data can be generated.

The method of the present invention provides an uncomplicated but highly effective procedure for analyzing the volatile components of a liquid stream by partitioning such component into a gaseous phase during segmented gas/liquid flow and then separating the gaseous phase from the segmented flow following which the gaseous phase is analyzed to identify the volatile components and concentrations thereof. Additionally, the apparatus of the invention functions as a useful interface between a water stream and a gas chromatograph for the on-line identification of volatile components and concentrations thereof in water.

What is claimed is:

1. A method of analyzing a first fluid for the presence therein of at least one volatile compound, said method comprising:
    (a) establishing a unidirectional, confined, flowing stream of segments of said first fluid separated by segments of a second fluid into which said compound is partitionable;
    (b) maintaining said stream flowing for a distance sufficient to enable partitioning of said compound from the segments of said first fluid into the segments of said second fluid;
    (c) separating the segments of said first and second fluids; and
    (d) analyzing the separated segments of said second fluid for determining the content therein of said compound.

2. The method of claim 1 wherein the segments of said first fluid are liquid and the segments of said second fluid are gas.

3. The method of claim 2 including dehumidifying the separated gas segments prior to the analysis thereof.

4. The method of claim 3 including separating the gas segments from the liquid segments via a membrane phase separator.

5. The method of claim 4 including analyzing the separated gas segments via gas chromatography.

6. The method of claim 3 including transferring the volatile compound of the liquid segments to the gas segments primarily during the flowing of said stream.

7. The method of claim 2 including analyzing the separated gas segments via gas chromatography.

8. The method of claim 7 wherein the compound detected is divided by its respective enrichment factor to determine the concentration thereof in said liquid segments.

9. The method of claim 8 wherein said enrichment factor is within the range of from 1 to 100.

10. The method of claim 8 wherein said enrichment factor is within the range of 1.7 to 76.

11. The method of claim 2 including transferring the volatile compounds of the liquid segments to the gas segments primarily during the flowing of said stream.

12. The method of claim 11 including analyzing the separated gas segments via gas chromatography.

13. The method of claim 2 including separating the gas segments from the liquid segments by debubbling said stream.

14. The method of claim 2 including separating the gas segments from the liquid segments via a membrane phase separator.

15. The method of claim 14 wherein the membrane phase separator is formed from microporous polypropylene.

16. The method of claim 2 including dehumidifying the separated gas segments prior to their analysis.

17. The method of claim 16 wherein the dehumidification of the separated gas segments includes removing water vapor from the gas segments by transferring the water vapor through a microporous membrane formed from a product of perfluorosulfonic acid.

18. The method of claim 2 including subjecting the separated gas segments to flow-through purging action.

19. The method of claim 2 wherein separating said liquid and gas segments includes flowing the stream of gas and liquid segments into a chamber having an upper gas outlet and a lower liquid trap, collecting and draining the liquid from liquid segments through the trap while forming a headsapce above the liquid in the chamber, and collecting the gas in the headspace.

20. The method of claim 2 wherein said analyzing step includes analyzing the separated gas segments by microchip gas chromatography.

21. Apparatus for the analysis of volatile compounds in a first fluid, said apparatus comprising:
    (a) partitioning means for establishing a flowing stream composed of segments of the first fluid spaced by segments of a second fluid which partition the volatile compounds into the second fluid from the first fluid;
    (b) separating means for separating the segments of the second fluid from said stream;
    (c) analyzing means for analyzing said separated segments of the second fluid to identify volatile compounds therein, and
    d) means for delivering said separated segments of the second fluid to said analyzing means.

22. The apparatus of claim 21 wherein said separating means includes a hollow microporous fiber.

23. The apparatus of claim 22 wherein said fiber is formed of polytetrafluoroethylene.

24. The apparatus of claim 22 wherein said separating means includes a second microporous hollow fiber accommodated within the first mentioned fiber.

25. The apparatus of claim 24 wherein said second fiber is formed of a perfluorosulfonic acid product.

26. The apparatus of claim 24 wherein the first fluid is a liquid and the second fluid is a gas, said fibers extending through a separation chamber, said first mentioned fiber being in communication with stream input means and liquid discharge means; and sampling port means establishing communication between said chamber and the interior of said second fiber.

27. The apparatus of claim 21 wherein said separating means includes a film of microporous polypropylene.

28. The apparatus of claim 21 wherein said partitioning means for establishing said flowing stream includes a peristaltic pump.

29. The apparatus of claim 21 wherein the first fluid is a liquid and the second fluid is a gas, said apparatus further including dehumidifying means acting on said separated gas segments prior to analysis thereof.

30. The apparatus of claim 21 wherein the first fluid is a liquid and the second fluid is a gas, said analyzing means comprising a gas chromatograph.

31. The apparatus of claim 30 wherein said gas chromatograph is a microchip gas chromatography system.

32. The apparatus of claim 31 wherein said separating means is formed of microporous polytetrafluoroethylene.

33. The apparatus of claim 21 including flow-through purging means.

34. The apparatus of claim 21 wherein said separating means is formed of microporous polypropylene.

35. The apparatus of claim 21 wherein said separating means is formed partly of microporous polypropylene and partly of microporous polytetrafluoroethylene.

36. The apparatus of claim 21 wherein the first fluid is a liquid and the second fluid is a gas, said separating means including a chamber having an upper gas outlet and a lower liquid trap, the liquid trapped in the chamber forming a headspace thereabove within the chamber for collecting the gas therein.

37. The apparatus of claim 36 wherein said chamber includes a gas outlet from said headspace to an outer environment, said apparatus including pumping means for continually pumping the liquid and gas segments through said system, said lower liquid trap and said gas outlet allowing for continued exhaust of liquid and gas for continual real time analysis of subsequent segments flowing under positive pressure from said pumping means to said chamber.

* * * * *